United States Patent
Shiota et al.

(10) Patent No.: US 6,314,158 B1
(45) Date of Patent: Nov. 6, 2001

(54) DATA PROCESSOR FOR FLUORESCENT X-RAY SPECTROSCOPY

(75) Inventors: Tadahiro Shiota; Makoto Nishino, both of Kyoto; Shoji Kuwabara, Osaka, all of (JP)

(73) Assignee: Shimadzu Corporation (JP)

( * ) Notice: Subject to any disclaimer, the term of this patent is extended or adjusted under 35 U.S.C. 154(b) by 0 days.

(21) Appl. No.: 09/521,243

(22) Filed: Mar. 8, 2000

(30) Foreign Application Priority Data

May 20, 1999 (JP) .................................................. 11-140413

(51) Int. Cl.⁷ .................................................. G01N 23/223
(52) U.S. Cl. .................................................. 378/48; 378/49
(58) Field of Search .................................. 378/48, 44, 45, 378/90, 49

(56) References Cited

U.S. PATENT DOCUMENTS 5,978,442 * 11/1999 Kuwabara .............................. 378/49
6,173,036 * 1/2001 Hossain et al. .......................... 378/45

* cited by examiner

*Primary Examiner*—Drew Dunn
(74) *Attorney, Agent, or Firm*—Coudert Brothers

(57) ABSTRACT

A data processor for fluorescent x-ray spectroscopy calculates theoretical x-ray intensity which is theoretically expected to be obtained by a fluorescent x-ray spectroscopy measurement of a standard sample with known composition by taking into account the effects of x-ray attenuation by the possible presence of an environmental gas along the optical path of the x-rays between the x-ray tube and the sample and between the sample and the detector. The element sensitivity for each of elements in the standard sample is obtained from this calculated x-ray intensity and the intensity actually measured and is stored in a memory. When a fluorescent x-ray spectroscopy measurement is carried out on an unknown sample, the sample is quantitatively analyzed, a theoretically calculated x-ray intensity obtained also by taking into account the effects of x-ray attenuation by an environmental gas is used together with the actually measured x-ray intensity and the element sensitivities stored in the memory.

5 Claims, 2 Drawing Sheets

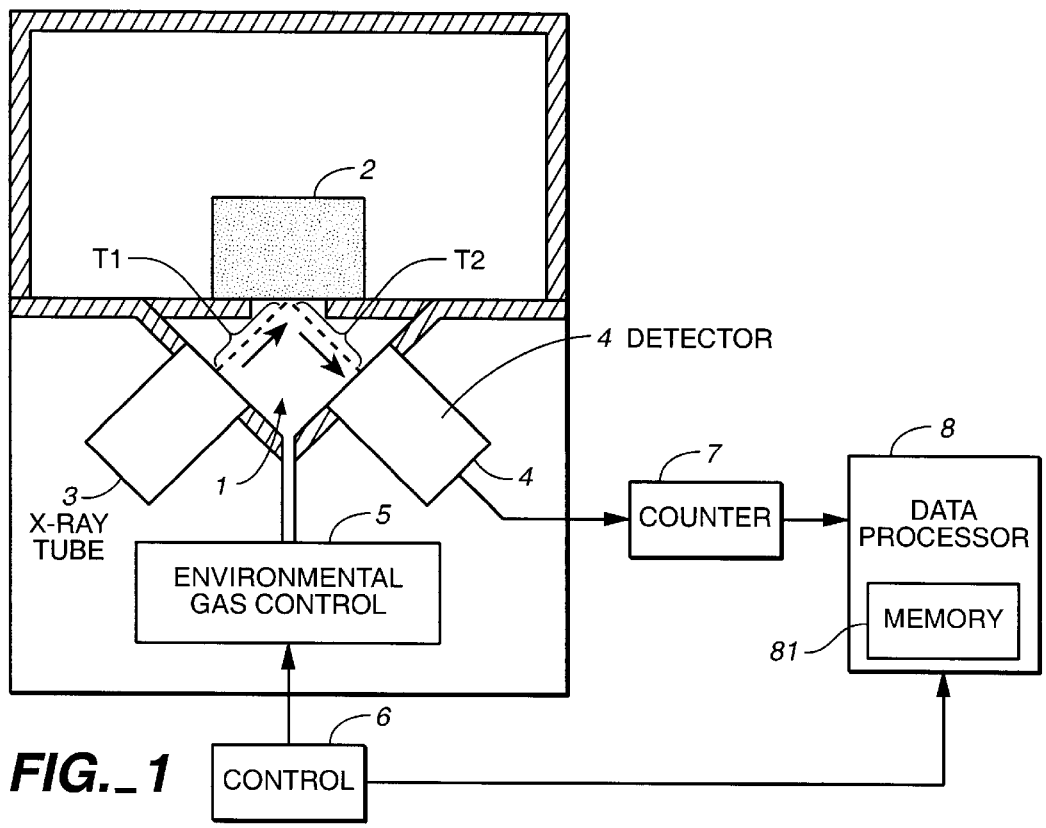
FIG._1
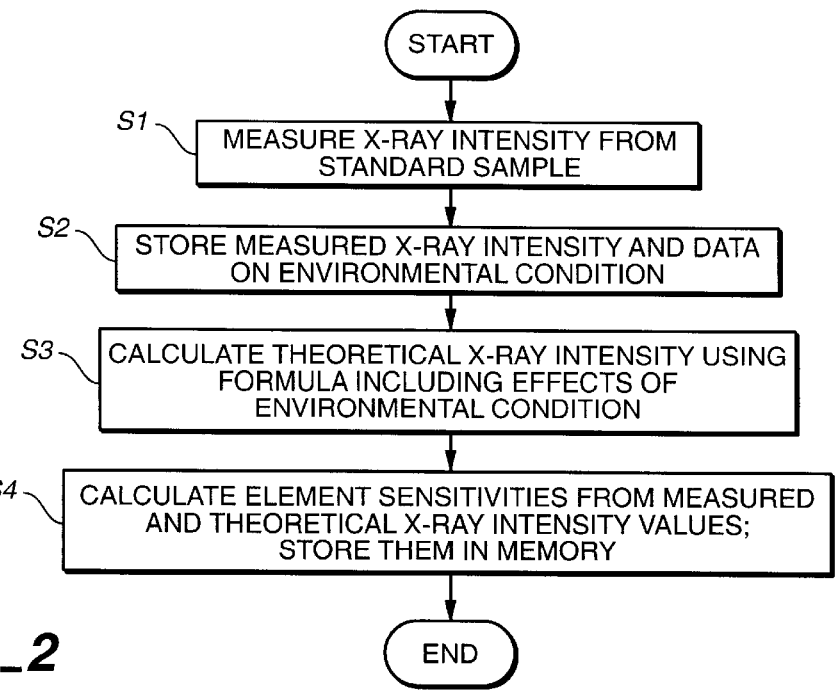
FIG._2

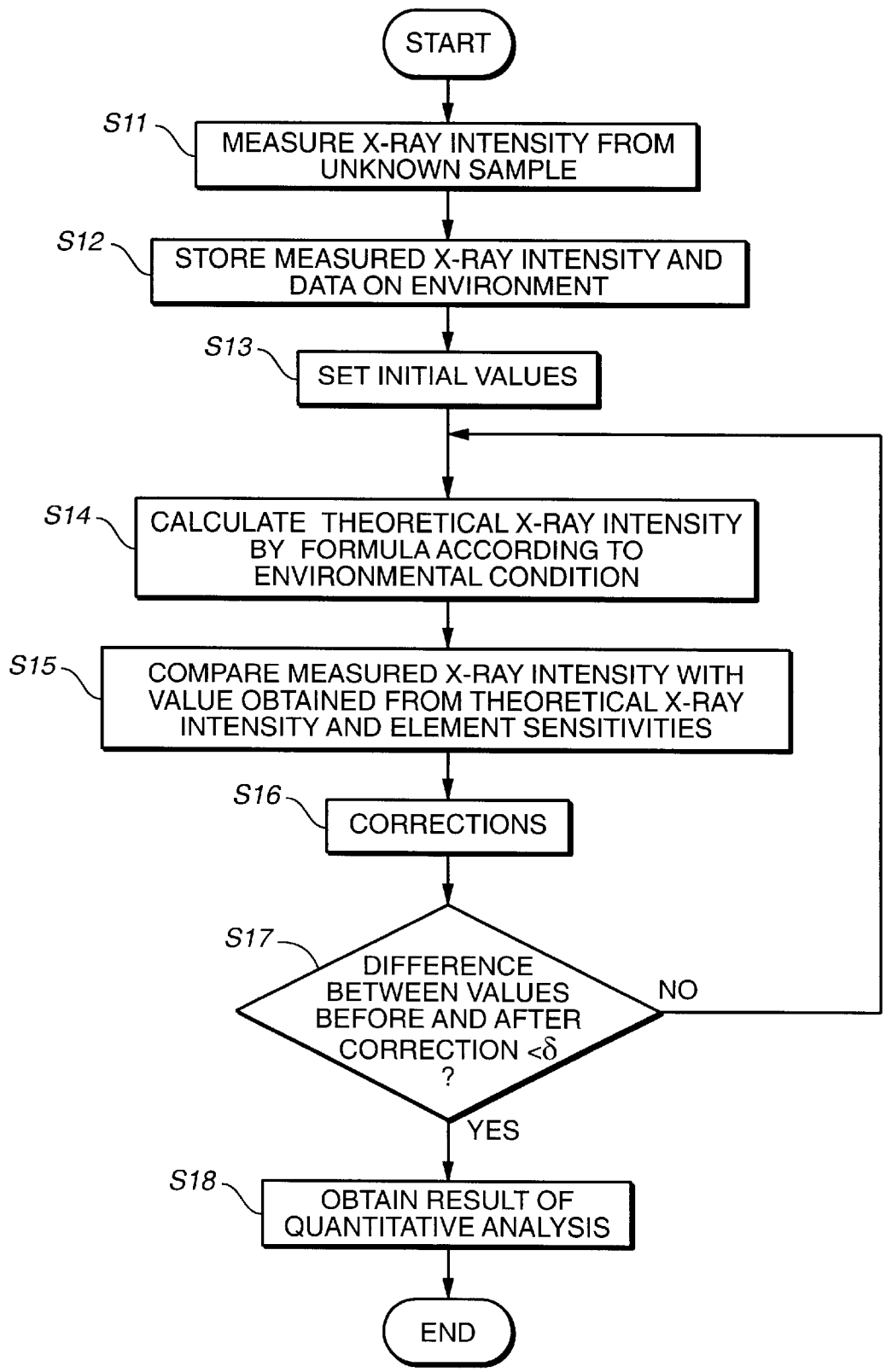
FIG._3

DATA PROCESSOR FOR FLUORESCENT X-RAY SPECTROSCOPY

BACKGROUND OF THE INVENTION

This invention relates to a data processor to be used in fluorescent x-ray spectroscopy, and in particular to a data processor for carrying out a quantitative analysis by making use of results of an x-ray fluorescence analysis.

In the field of fluorescent x-ray spectroscopy, quantitative analyses by using the so-called fundamental parameter (FP) method are recently coming to be widely carried out. This method of analysis is characterized wherein the contents of the elements in a sample are determined on the basis of both the measured intensity of fluorescent x-ray emitted from the sample and a theoretically calculated x-ray intensity value. When such a method of analysis is used, many parameters are necessary for calculating the theoretical x-ray intensity. Examples of such parameters include the accelerating voltage of current for the primary x-rays applied from an x-ray tube to the sample, the contents of all elements contained in the sample, their physical constants such as the atomic numbers and wavelengths of fluorescence, the angle of incidence of the primary x-rays onto the sample and the angle of measured fluorescent x-rays from the sample. The x-ray intensity theoretically calculated on the basis of these parameters is that of the fluorescent x-rays as they are generated on the surface of the sample. The measured intensity, on the other hand, is obtained after the fluorescent x-rays generated on the surface of the sample reaches a detector and is thereby converted into electrical energy pulses. For this reason, the theoretically obtained x-ray intensity and the measured intensity do not always agree as a matter of course. For this reason, what is commonly being done is to preliminary make measurements on a standard sample of which the composition is known, to calculate and store the ratio between the measured and theoretical intensities for each element (usually referred to as the "element sensitivity") and to carry out the usual steps of quantitative analysis while making appropriate adjustments by using such element sensitivities.

In fluorescent x-ray spectroscopy, it is desired to make the degree of vacuum inside the analysis chamber as high as possible because any gas which is present along the optical path of the primary x-rays between the x-ray tube and the sample and that of the fluorescent x-rays generated on the surface of the sample between the sample and the detector acts to absorb the x-rays to attenate the intensity. When the sample is a liquid or in a powder form and is easy to scatter around and if it is difficult to maintain a vacuum environment inside the analysis chamber, it is inevitable to carry out the analysis either in an atmospheric environment or in an environment of helium or some other appropriate kind of gas.

If measurements are taken under such a condition, x-rays are attenuated both between the x-ray tube and the sample and between the sample and the detector. In other words, the measured intensity values include the effects of x-ray absorption while theoretically calculated values are those of the intensity on the sample surface without taking the effects of attenuation by absorption into account.

In view of the above, the standard sample had to be measured under different conditions such as in vacuum, under the atmospheric condition and in helium and to prelimarily obtain the element sensitivities as measured under different conditions from the results of such measurements. For the quantitative analysis of a given sample with an unknown composition, a theretical calculation had to be carried out by using a correct element sensitivity corresponding to the environment in which the measurement was taken. It now goes without saying that this routine is troublesome and cumbersome because it involves obtaining many element sensitivities and storing many sensitivity data.

This problem is particularly important with lighter elements with small molecular values because fluorescent x-rays emitted from such light elements are particularly susceptible to absorption by an environmental gas. If the measurement must be taken in an atmospheric environment or in helium, for example, the intensity of the x-rays reaching the detector may be quite weak and a trustworthy analysis cannot be expected to result if an inaccurate element sensitivity must be used.

SUMMARY OF THE INVENTION

It is therefore an object of this invention to provide a data processor for fluorescent x-ray spectroscopy with which the troubles for obtaining element sensitivities can be eliminated and the accuracy of analysis can be improved.

A data processor for fluorescent x-ray spectroscopy with which the above and other objects can be attained is characterized wherein theoretical x-ray intensity values from a standard sample with a known composition and an unknown sample with an unknown composition are calculated by using a formula which incorporates the effect of x-ray absorption by an environmental gas which may be present inside the analysis chamber. Thus, the element sensitivity calculated on the basis of the result of measurement on a standard sample according to this invention is a value which is independent of the environmental condition inside the analysis chamber when the measurement was taken.

Explained more in detail, a data processor for fluorescent x-ray spectroscopic measurement functions such that theoretical x-ray intensity expected to be obtained by measurement on a standard sample with known composition is calculated by using a formula which incorporates the effects of the environmental condition inside the analysis chamber, that is, the possible effects of x-ray attenuation if the interior of the analysis chamber is not in a vacuum condition. Element sensitivity values are obtained from such calculated intensity and the result of an actual measurement on the standard sample. When an unknown sample with unknown composition is to be analyzed similarly by fluorescent x-ray spectroscopy, a theoretical x-ray intensity value is calculated, say, by initially using estimated values as parameters and using the formula incorporating the effects of the environmental condition inside the analysis chamber on the attenuation of the x-rays. Actually measured intensity and theoretically obtained intensity values are compared and the parameters are changed, if their difference is larger than a specified maximum allowable limit value, and this process may be repeated any number of times until it becomes satisfactorily small, or less than a specified allowable limit. The composition of the unknown sample is obtained from the theoretically calculated intensity, actually measured intensity and the element sensitivity which was earlier obtained.

BRIEF DESCRIPTION OF THE DRAWINGS

The accompanying drawings, which are incorporated in and form a part of this specification, illustrate an embodiment of the invention and, together with the description, serve to explain the principles of the invention. In the drawings:

FIG. 1 is a block diagram of a fluorescent x-ray spectroscope incorporating a data processor embodying this invention;

FIG. 2 is a flow chart of a routine for obtaining an element sensitivity by the data processor of this invention; and FIG. 3 is a flow chart of a routine for quantitatively analyzing an unknown sample by the data processor of this invention.

DETAILED DESCRIPTION OF THE INVENTION

The invention is described next by way of an example with reference to FIG. 1 wherein numeral 1 indicates an analysis chamber of which the upper wall serves as a base plate for carrying a sample 2 thereon. An x-ray tube 3 and a detector 4 for detecting x-rays over all wavelengths are attached to obliquely oriented lower walls of the analysis chamber 1. The interior of the analysis chamber 1 communicates with an environment changing apparatus 5 including a vacuum pump, serving not only to provide a vacuum environment inside the analysis chamber 1 but also to introduce a specified kind of environmental gas such as helium, if necessary, in response to a command from a control unit 6. The detector 4 may be a semiconductor detector and serves to output a pulse signal corresponding to the intensity of the incident x-rays. The pulse signals are counted by a counter 7 which serves to output an electric signal corresponding to the x-ray intensity to a data processor 8. The data processor 8 may comprise a personal computer of a known kind but is adapted to carry out a specified program to be described below for quantitative analysis.

The method of computation carried out by the data processor 8 is explained next in detail. When a beam of primary x-rays with wavelength $\lambda$ is made incident on a sample, the theoretical intensity $I(ip)$ of fluorescent x-rays generated on the sample surface is known to be given as follows:

$$I(ip) = (1/\sin\theta) \int_{x=0}^{x=\infty} \int_{\lambda_{min}}^{\lambda_{ie}} I_0(\lambda) Q_{ip}(\lambda) dx d\lambda \quad (1)$$

where $$Q_{ip}(\lambda) = W_i \mu_i(\lambda) K_i \omega_i R_{pi},$$

i is a parameter indicating an element, p is another parameter indicating the kind of spectral line (such as $K_\alpha$, $K_\beta$, and $L_\alpha$), x is the distance in the direction of thickness of the sample, $\lambda_{min}$ is the shortest wavelength of the primary x-rays, $\lambda_{ie}$ is the absorption end wavelength of element i, $W_i$ is the content of element i, $\mu_i(\lambda)$ is the coefficient of mass absorption of x-rays with wavelength $\lambda$ by element i, $K_i$ is the so-called jump ratio or absorption jump of element i, $\omega_i$ is the fluorescent yield of element i (that is, the ratio of fluorescent x-ray generation with respect to the entire excitation in the series to which the p-line of element i belongs), $R_{pi}$ is the intensity fraction of the ip-line in the characteristic x-ray series to which it belongs, $I_0(\lambda)$ is the intensity of the primary x-rays with wavelength $\lambda$, and $\theta$ is the angle between the direction of incidence of the primary x-rays and the surface of the sample.

Formula (1) is applicable to the fluorescent x-ray spectroscope as shown in FIG. 1 when the interior of the analysis chamber 1 is in a vacuum condition and absorption of the x-rays (both the primary x-rays and the fluorescent x-rays) need not be considered. According to the present invention, by contrast, the expression for the intensity of the primary x-rays (given by $I_0(\lambda)$ in Formula (1) above) is replaced, if the interior or the analysis chamber 1 is not a vacuum, by another expression $I_0'(\lambda)$ given below which takes into account the attenuation caused by the environmental gas along the optical path between the x-ray tube 3 and the sample 2 (say, of length $T_1$ therein):

$$I_0'(\lambda) = I_0(\lambda) \exp\{-\mu_{Pi(\lambda)} \rho_{Pi} T_1\} \quad (2)$$

where $\mu_{Pi(\lambda)}$ is the coefficient of mass absorption of the x-rays of wavelength $\lambda$ by the environmental gas and $\rho_{Pi}$ is the density of the environmental gas. In other words, (1) is replaced by the following:

$$I(ip) = I_0(\lambda) \exp\{-\mu_{Pi(\lambda)} \rho_{Pi} T_1\} d\lambda Q_{ip}(\lambda) dx / \sin\theta \quad (3)$$

Since the expression given by Formula (3) above represents the theoretical intensity of the fluorescent x-rays at the surface of the sample 2, the effect of attenuation due to the presence of the environmental gas between the sample 2 and the detector 4 (separated by a distance, say, of $T_2$) must be taken into account to obtain the theoretical intensity $I'(ip)$ of the fluorescent x-rays reaching the detector 4 as follows:

$$I'(ip) = I(ip) \exp\{-\mu_{Pi(\lambda)} \rho_{Pi} T_2\}. \quad (4)$$

The relationship between the actually measured x-ray intensity M and the theoretical x-ray intensity I (that is, $I(ip)$ or $I'(ip)$, depending on the environmental condition) may be simply expressed as follows:

$$M = fI \quad (5)$$

where f is the element sensitivity although a more complicated functional relationship may be used if a more exact result is desired.

The formula which is necessary for calculating a theoretical value of the x-ray intensity is already incorporated in the program of the data processor 8 for carrying out a quantitative analysis. A practical example of carrying out such a quantitative analysis by means of such a program will be explained next with reference to the flow chart of FIG. 2 for deriving the element sensitivity and the flow chart of FIG. 3 for a routine for quantitative analysis.

For obtaining element sensitivities, fluorescent x-rays of a standard sample with known composition are measured (Step S1). This is usually done in a vacuum environment but a specified kind of gas such as the atmospheric air or helium may be introduced by means of the environment changing apparatus 5 if this is necessary. The data on the measured x-ray intensity are transmitted from the counter 7 and stored temporarily in a memory device 81 of the data processor 8. Data on the environment (such as the kind of the environmental gas) at the time of the measurement are provided by the control unit 6 and are also stored in the memory 81 in correlation with the measured x-ray intensity data (Step S2).

Next, the data processor 8 undertakes to calculate the theoretical intensity of the fluorescent x-ray spectrum. This is done firstly by identifying the condition of the environment from the data stored in its memory 81 and Formula (1) above is used if the measurement was in a vacuum environment and Formulas (3) and (4) if it is otherwise (Step S3). In other words, if there is an environmental gas present, the theoretical fluorescent x-ray intensity is calculated with the effects of the x-ray attenuation taken into account. Element sensitivities are calculated from the theoretical x-ray intensity and actually measured x-ray intensity by using Formula (5) and are stored in the memory 81 (Step S4).

When a sample with unknown composition is quantitatively analyzed, a measurement of fluorescent x-ray from this unknown sample is taken first (Step S11). For this measurement, too, the environmental condition inside the analysis chamber 1 can be appropriately controlled by means of the environment changing apparatus 5. As data on the measured x-ray intensity are transmitted from the counter 7 and stored temporarily in the memory 81 of the data processor 8. Data on the environment (such as the kind of the environmental gas) at the time of the measurement are provided by the control unit 6 and are also stored in the memory 81 in correlation with the measured x-ray intensity data (Step S12). As a routine for quantitative analysis is started by the data processor 8, an appropriate value for each constituent component ("initial estimate of mass fraction") is initially set (Step S13). There are different ways for setting such an initial value. Any of such methods may be employed, and theoretical x-ray intensity values are calculated on the basis of these initial estimates that have been set. For this step, too, as in Step S3 described above, the data on the environmental condition stored in the memory 81 are used, and Formula (1) is used if it is a vacuum while Formulas (3) and (4) are used if otherwise (Step S14). In other words, if there is an environmental gas present, the theoretical fluorescent x-ray intensity is calculated with the effects of the x-ray attenuation taken into account.

According to Formula (5), the theoretical x-ray intensity value multiplied by the element sensitivity should equal the actually measured x-ray intensity value. Thus, the theoretically calculated x-ray intensity thus obtained is multiplied by the element sensitivity stored in the memory 81 and the produce of this multiplication is compared with the actually measured value (Step S15). The closer the initial estimates represent the actual composition, the product obtained as described above should be closer to the actually measured x-ray intensity. In the next step, the initial estimates are modified, or corrected, by using a suitable algorithm on the basis of the difference obtained by this comparison (Step S16). The values before and after this correction is calculated, and if this difference is smaller than a preliminarily specified threshold value (or a maximum allowable difference value) δ, (YES in Step S17), the set value is considered to have converged sufficiently close to the real value and this value is considered as the final result (Step S18). If the difference thus calculated is larger than the convergence limit δ (NO in Step S17), the routine goes back to Step S14 and another theoretical x-ray intensity value is calculated by using the corrected value. As this routine is repeated, the calculated value will converge to the real value. Since the number of repetitions will be smaller if the initial estimates are closer to the real values, it is desirable to select the algorithm appropriately such as disclosed in an article entitled "Calculation Methods for Fluorescent X-Ray Spectrometry" by J. W. Criss and L. S. Birks which appeared in Analytical Chemistry, Vol. 40, No. 7 (June, 1968) at page 1080.

Although the invention has been described above by way of only one example, the invention is not intended to be bound by this example. Many modifications and variations are possible within the scope of the invention. In summary, a date processor according to the present invention takes into consideration the effects of environmental gas which may be present at time of the measurement such that an accurate quantitative analysis can be carried out even if there is an environmental gas such as the atmospheric gas or helium. In practice, it is sufficient to measure a standard sample under any environmental condition in order to obtain element sensitivities, unlike according to prior art technology whereby measurements had to be taken under different environmental conditions. Thus, the measurement of a standard sample can be carried out much more easily. Since element sensitivities are often the same under many different environmental conditions, the amount of data to be stored need not be large.

What is claimed is:

1. A data processor for fluorescent x-ray spectroscopy, said data processor comprising:

first calculating means for calculating first theoretical x-ray intensity which is theoretically expected to be obtained from a first measurement in fluorescent x-ray spectroscopy of a standard sample with known composition inside a chamber by taking into account x-ray attenuation according to environmental condition inside said chamber when said first measurement was taken;

sensitivity-calculating means for calculating element sensitivities for elements in said standard sample from said first theoretical x-ray intensity calculated by said first calculating means and measured intensity obtained by actually measuring said standard sample by fluorescent x-ray spectroscopy;

memory means for storing said calculated element sensitivities;

second calculating means for calculating second theoretical x-ray intensity which is theoretically expected to be obtained from a second measurement in fluorescent x-ray spectroscopy of an unknown sample by taking into account x-ray attenuation according to environmental condition inside said chamber when said second measurement was taken; and analyzing means for calculating content of each component contained in said unknown sample from said second theoretical x-ray intensity, measured intensity obtained by actually measuring said unknown sample by fluorescent x-ray spectroscopy and said element sensitivities stored in said memory means.

2. The data processor of claim 1 further comprising an environmental control means for controlling said environmental condition inside said chamber under which said first measurement and said second measurement are taken.

3. The data processor of claim 2 wherein said environmental condition includes presence and absence of a gas inside said chamber and the type of said gas, if present.

4. The data processor of claim 2 further comprising means for causing data on said environmental condition to be stored in said memory means.

5. The data processor of claim 1 wherein said second theoretical x-ray intensity is calculated by using initial estimates of mass fraction to obtain an initial value, calculating a difference between the measured intensity of said unknown sample and the product of said initial value and said element sensitivities stored in said memory means, making a comparison between said difference with a specified maximum allowable difference value, and repeating calculation of said second theoretical x-ray intensity, depending on result of said comparison, by making corrections on said initial estimates.

* * * * *